(12) United States Patent
Bateman et al.

(10) Patent No.: US 11,398,329 B2
(45) Date of Patent: Jul. 26, 2022

(54) PARTIAL INSULATION WITH DIAGNOSTIC PICKUP COILS

(71) Applicant: Tokamak Energy Ltd, Abingdon (GB)

(72) Inventors: Rod Bateman, Abingdon (GB); Robert Slade, Abingdon (GB); Bas Van Nugteren, Abingdon (GB)

(73) Assignee: Tokamak Energy Ltd., Abingdon (GB)

(*) Notice: Subject to any disclaimer, the term of this patent is extended or adjusted under 35 U.S.C. 154(b) by 0 days.

(21) Appl. No.: 17/594,073

(22) PCT Filed: Mar. 31, 2020

(86) PCT No.: PCT/EP2020/059184
§ 371 (c)(1),
(2) Date: Oct. 1, 2021

(87) PCT Pub. No.: WO2020/201316
PCT Pub. Date: Oct. 8, 2020

(65) Prior Publication Data
US 2022/0148778 A1    May 12, 2022

(30) Foreign Application Priority Data
Apr. 1, 2019  (GB) .................................. 1904528

(51) Int. Cl.
*H01F 6/06*    (2006.01)
*A61N 5/10*    (2006.01)
(Continued)

(52) U.S. Cl.
CPC ............ *H01F 6/06* (2013.01); *A61N 5/1077* (2013.01); *G21K 1/093* (2013.01); *G21K 5/04* (2013.01);
(Continued)

(58) Field of Classification Search
CPC ........... H01F 6/06; H01F 6/02; A61N 5/1077; A61N 2005/1087; G21K 1/093; G21K 5/04; H05H 7/04; H05H 2277/11
See application file for complete search history.

(56) References Cited

U.S. PATENT DOCUMENTS 5,026,682 A * 6/1991 Clark .................... H01L 39/225
427/63
5,187,859 A * 2/1993 Heim .................... H01F 41/048
29/605

(Continued)

FOREIGN PATENT DOCUMENTS

| EP | 2363897 A1 | 9/2011 |
|---|---|---|
| GB | 1101652 A | 1/1968 |
| WO | 2019150123 A1 | 8/2019 |

OTHER PUBLICATIONS

International Search Report and Written Opinion for Application No. PCT/EP2020/059184 dated Jun. 24, 2020 (18 pages).

(Continued)

*Primary Examiner* — David A Vanore
(74) *Attorney, Agent, or Firm* — Michael Best & Friedrich LLP

(57) ABSTRACT

A partially insulating layer for use in an HTS magnet coil. The partially insulating layer comprises an insulating body 401 having within it a set of linking tracks and a set of pickup tracks. Each linking track is electrically conductive and is electrically connected to first and second surfaces of the partially insulating layer, in order to provide an electrical path between said first and second surfaces. Each pickup track is electrically conductive and is inductively coupled to a respective linking track, and electrically isolated from the first and second surfaces. Each of the pickup tracks is configured for connection to a current measuring device in (Continued)

order to measure a current induced in the pickup track by a change in current flowing in the respective linking track.

20 Claims, 6 Drawing Sheets

(51) Int. Cl.
  *G21K 5/04*    (2006.01)
  *H05H 7/04*    (2006.01)
  *G21K 1/093*   (2006.01)
  *H01F 6/02*    (2006.01)

(52) U.S. Cl.
  CPC ....... *H05H 7/04* (2013.01); *A61N 2005/1087* (2013.01); *H01F 6/02* (2013.01); *H05H 2277/11* (2013.01)

(56) References Cited

U.S. PATENT DOCUMENTS

| | | | | |
|---|---|---|---|---|
| 5,869,846 | A * | 2/1999 | Higashino | H01L 39/225 257/E39.015 |
| 6,376,775 | B1 * | 4/2002 | Leijon | H01F 3/14 174/128.1 |
| 7,046,492 | B2 * | 5/2006 | Fromm | H01F 27/288 361/38 |
| 2009/0046399 | A1 | 2/2009 | Kurusu et al. | |
| 2010/0197505 | A1 * | 8/2010 | Steinmeyer | H01L 39/2464 505/433 |
| 2013/0057267 | A1 | 3/2013 | Klein | |
| 2014/0066314 | A1 * | 3/2014 | Maeda | C08G 73/106 174/110 SR |
| 2017/0016937 | A1 | 1/2017 | Riehl et al. | |
| 2019/0252754 | A1 * | 8/2019 | Mueller | H01P 1/387 |
| 2021/0183552 | A1 * | 6/2021 | Chorley | H01F 6/04 |

OTHER PUBLICATIONS

International Preliminary Report on Patentability for Application No. PCT/EP2020/059184 dated Mar. 10, 2021 (16 pages).

Lee et al., "The effects of co-wound Kapton, stainless steel and copper, in comparison with no insulation, on the time constant and stability of GdBCO pancake coils", Superconductor Science and Technology, vol. 27, 2014, 8 pages.

Hasegawa et al., "Fundamental Evaluations of Applicability of LTS Quench Detectors to REBCO Pancake Coil", IEEE Transactions on Applied Superconductivity, vol. 29, No. 5, 2019, pp. 1-5.

* cited by examiner

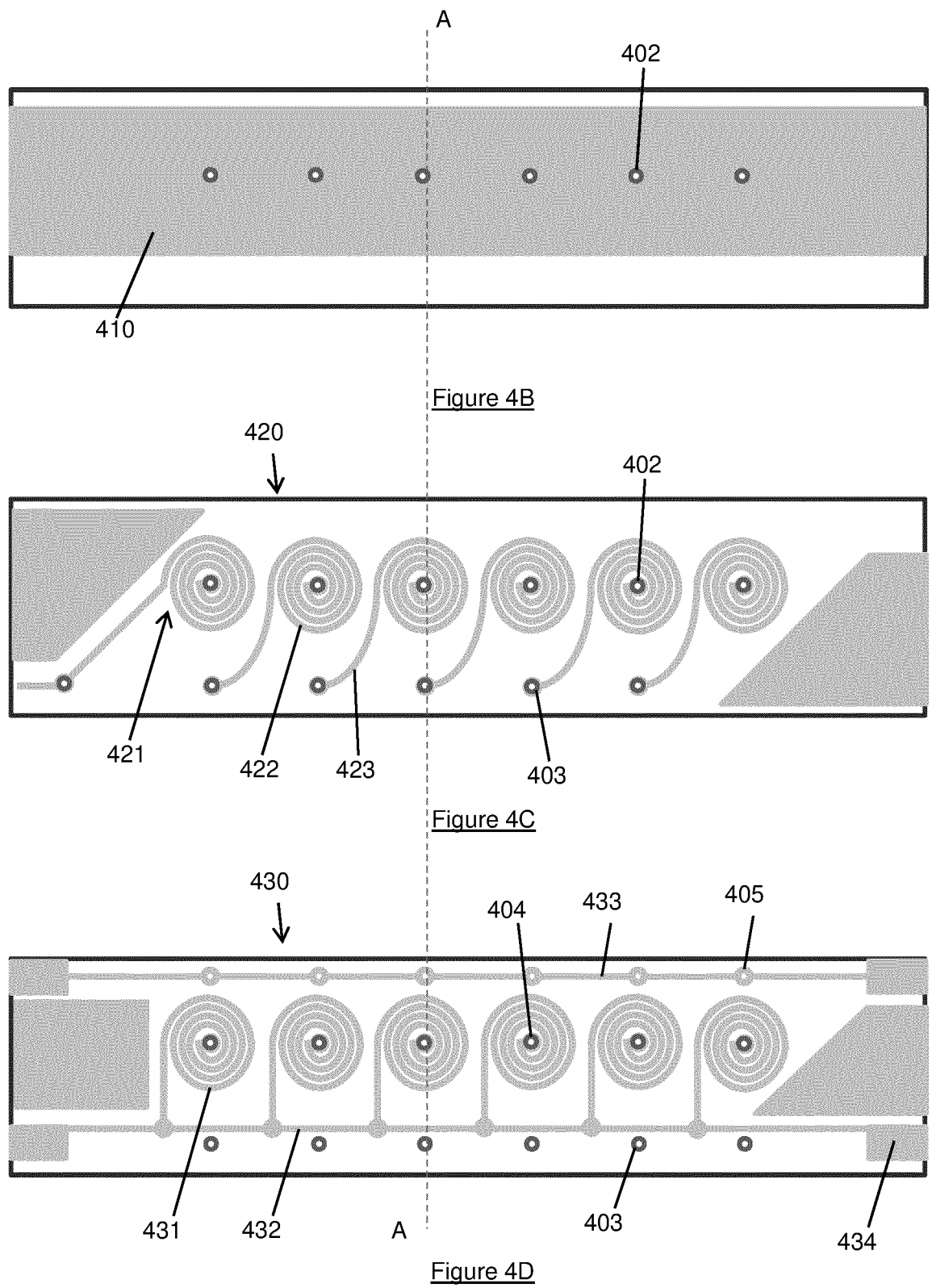

PARTIAL INSULATION WITH DIAGNOSTIC PICKUP COILS

CROSS-REFERENCE TO RELATED APPLICATION(S)

This application is a national phase entry of PCT/EP2020/059184, filed on Mar. 31, 2020, which claims priority to GB 1904528.5, filed on Apr. 1, 2019, the entire contents of each of which are fully incorporated herein by reference.

FIELD OF THE INVENTION

The present invention relates to high temperature superconducting (HTS) magnets. In particular, the invention relates to a partially insulating layer for use in a partially insulated HTS magnet.

BACKGROUND

Superconducting materials are typically divided into "high temperature superconductors" (HTS) and "low temperature superconductors" (LTS). LTS materials, such as Nb and NbTi, are metals or metal alloys whose superconductivity can be described by BCS theory. All low temperature superconductors have a critical temperature (the temperature above which the material cannot be superconducting even in zero magnetic field) below about 30K. The behaviour of HTS material is not described by BCS theory, and such materials may have critical temperatures above about 30K (though it should be noted that it is the physical differences in composition and superconducting operation, rather than the critical temperature, which define HTS and LTS material). The most commonly used HTS are "cuprate superconductors"-ceramics based on cuprates (compounds containing a copper oxide group), such as BSCCO, or ReBCO (where Re is a rare earth element, commonly Y or Gd). Other HTS materials include iron pnictides (e.g. FeAs and FeSe) and magnesium diborate ($MgB_2$).

ReBCO is typically manufactured as tapes, with a structure as shown in FIG. 1. Such tape 100 is generally approximately 100 microns thick, and includes a substrate 101 (typically electropolished hastelloy approximately 50 microns thick), on which is deposited by IBAD, magnetron sputtering, or another suitable technique a series of buffer layers known as the buffer stack 102, of approximate thickness 0.2 microns. An epitaxial ReBCO-HTS layer 103 (deposited by MOCVD or another suitable technique) overlays the buffer stack, and is typically 1 micron thick. A 1-2 micron silver layer 104 is deposited on the HTS layer by sputtering or another suitable technique, and a copper stabilizer layer 105 is deposited on the tape by electroplating or another suitable technique, which often completely encapsulates the tape.

The substrate 101 provides a mechanical backbone that can be fed through the manufacturing line and permit growth of subsequent layers. The buffer stack 102 is required to provide a biaxially textured crystalline template upon which to grow the HTS layer, and prevents chemical diffusion of elements from the substrate to the HTS which damage its superconducting properties. The silver layer 104 is required to provide a low resistance interface from the ReBCO to the stabiliser layer, and the stabiliser layer 105 provides an alternative current path in the event that any part of the ReBCO ceases superconducting (enters the "normal" state).

In addition, "exfoliated" HTS tape can be manufactured, which lacks a substrate and buffer stack, and instead has silver layers on both sides of the HTS layer. Tape which has a substrate will be referred to as "substrated" HTS tape.

HTS tapes may be arranged into HTS cables. An HTS cable comprises one or more HTS tapes, which are connected along their length by conductive material (normally copper). The HTS tapes may be stacked (i.e. arranged such that the HTS layers are parallel), or they may have some other arrangement of tapes, which may vary along the length of the cable. Notable special cases of HTS cables are single HTS tapes, and HTS pairs. HTS pairs comprise a pair of HTS tapes, arranged such that the HTS layers are parallel. Where substrated tape is used, HTS pairs may be type-0 (with the HTS layers facing each other), type-1 (with the HTS layer of one tape facing the substrate of the other), or type-2 (with the substrates facing each other). Cables comprising more than 2 tapes may arrange some or all of the tapes in HTS pairs. Stacked HTS tapes may comprise various arrangements of HTS pairs, most commonly either a stack of type-1 pairs or a stack of type-0 pairs and (or, equivalently, type-2 pairs). HTS cables may comprise a mix of substrated and exfoliated tape.

A superconducting magnet is formed by arranging HTS cables (or individual HTS tapes, which for the purpose of this description can be treated as a single-tape cable) into coils, either by winding the HTS cables or by providing sections of the coil made from HTS cables and joining them together. HTS coils come in three broad classes:
  Insulated, having electrically insulating material between the turns (so that current can only flow in the "spiral path" through the HTS cables).
  Non-insulated, where the turns are connected radially, as well as along the cables (e.g. by connecting the copper stabilising layers of the HTS cables).
  Partially insulated, where the turns are connected radially with a controlled resistance, either by the use of materials with a high resistance (e.g. compared to copper), or by providing intermittent insulation between the coils.

Non-insulated coils could also be considered as the low-resistance case of partially insulated coils.

Having no or partial insulation between turns slows the rate at which the temperature of a local "hotspot" (normal zone) rises. The rate of growth (spatial propagation) of a normal (resistive HTS) zone in an HTS magnet depends on many parameters, but is typically less than 100 mm/s in the axial direction (ie: along the cable), and roughly 2-100 times slower in the transverse direction (ie: between adjacent turns). The exact rate of propagation of the normal zone in each direction depends on the thermal and electrical properties of the materials and cable construction utilised. In particular, the rate of transverse propagation is affected by the thermal properties of the material between turns.

In a large magnet (linear dimensions of metres, and where the coil cross section dimensions are small (ie ~10 times less) than the largest overall coil dimension) the transverse propagation can cause the entire cross section of the coil to become normal in a zone covering a small fraction of the coil's periphery, resulting in the total current of all turns flowing only in the metal stabilizer within the normal section. Outside the normal zone the conductors are still superconducting. The resistance of this normal zone is not enough to cause the magnet's current to fall quickly but results in the stored magnetic energy of the whole magnet being dumped into this small normal (resistive) volume, which is only growing around the coil periphery slowly. Unless this situation is detected quickly so that the magnet's stored energy can be dumped into a resistance external to the coil, the temperature of the normal zone will rise very quickly, which is likely to cause significant damage to conductors within the normal zone.

One use of HTS magnets is in tokamak fusion reactors and plasma chambers, particularly in spherical tokamaks. A tokamak has two sets of magnets—poloidal field coils, which are aligned to produce a poloidal field and are generally circular, and toroidal field coils, which comprise a central column and a plurality of return limbs, and are arranged to produce a toroidal field. HTS magnets can be used for either set of field coils, but are particularly useful for toroidal field coils in small tokamaks, as such field coils have tight space limitations which the improved current density and/or reduced cooling requirements of HTS can help with significantly.

Another potential use of HTS magnets is in proton beam therapy devices. Proton beam therapy (PBT, also known as proton therapy) is a type of particle therapy used in the treatment of cancers (and other conditions which respond to radiotherapy). In PBT, a beam of protons is directed towards the treatment location (e.g. the tumour).

Another, similar therapy is proton boron capture therapy (PBCT), in which boron-11 is introduced to the target location, and a proton beam is used to initiate the $p+^{11}B \rightarrow 3\alpha$ reaction. The same apparatus can be used to provide proton beams for either PBT or PBCT.

The proton beams for PBT and PBCT are generated by particle accelerators such as a cyclotrons or linear accelerators. Accelerators typically used for PBT and PBCT typically produce protons with energies in the range of 60 to 250 MeV, with the most powerful currently operating facility having a maximum energy of 400 MeV.

The design of PBT or PBCT devices requires a gantry to hold electromagnets capable of steering protons at the beam energy. This requires very high magnetic fields, and as such the use of HTS magnets can considerably reduce the mass and size of the electromagnets and the gantry needed to move them. HTS magnets may be used within the accelerator, quadrupole magnets of the steering magnets, or dipole magnets of the steering magnets.

SUMMARY

According to a first aspect, there is provided a partially insulating layer for use in an HTS magnet coil. The partially insulating layer comprises an insulating body 401 having within it a set of linking tracks and a set of pickup tracks. Each linking track is electrically conductive and is electrically connected to first and second surfaces of the partially insulating layer, in order to provide an electrical path between said first and second surfaces. Each pickup track is electrically conductive and is inductively coupled to a respective linking track, and electrically isolated from the first and second surfaces. Each of the pickup tracks is configured for connection to a current measuring device in order to measure a current induced in the pickup track by a change in current flowing in the respective linking track.

According to a second aspect, there is provided a partially insulating layer for use in an HTS magnet coil. The partially insulating layer comprises an insulating body 701 having within it a set of linking tracks and a set of pickup tracks. Each linking track is electrically conductive and is electrically connected to first and second surfaces of the partially insulating layer, in order to provide an electrical path between said first and second surfaces. The pickup track is electrically conductive, extends along the length of the partially insulating layer, and is electrically isolated from the first and second surfaces. The pickup track is configured for connection to a voltage measuring device in order to measure a voltage induced in the pickup track by a change in current in an HTS conductor of the HTS magnet coil.

According to a third aspect, there is provided a high temperature superconducting, HTS, field coil comprising one or more HTS cables and one or more partially insulating layers, wherein the one or more HTS cables are arranged to form turns, and the one or more partially insulating layers are arranged to connect the turns radially, wherein the partially insulating layers are partially insulating layers according to the first or second aspect.

According to a fourth aspect, there is provided a tokamak comprising a toroidal field coil which is an HTS field coil according to the third aspect.

According to a fifth aspect, there is provided a proton beam therapy, PBT, device comprising an HTS field coil according to the third aspect, wherein the HTS field coil is one of:
a field coil of an accelerator of the PBT device;
a dipole or quadrupole magnet of a proton beam steering system of the PBT device.

BRIEF DESCRIPTION OF THE DRAWINGS

FIGS. 4A to F show an exemplary partially insulating layer.

DETAILED DESCRIPTION

Figure 1:
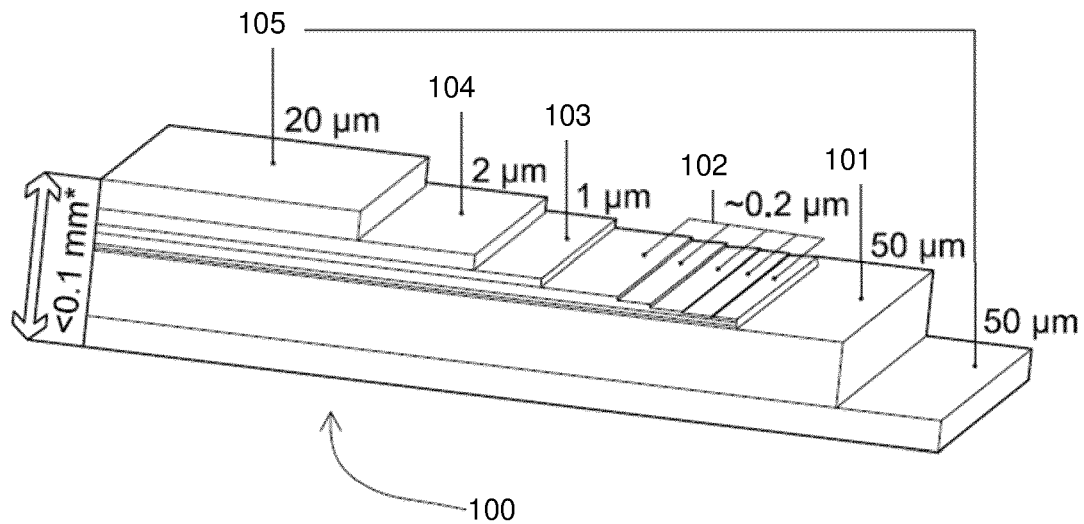
FIG. 1 is a schematic illustration of an HTS tape.

FIGS. 2A to E show a partially insulating layer which may be applied between HTS cables to connect them radially.

The partially insulating layer comprises 5 layers, which are, in order:
a first metal connection layer 211;
a first insulating layer 221;
an electrically conducting layer 230;
a second insulating layer 222;
a second metal connection layer 212.

FIGS. 2 C to E show the layout of the first metal connection layer 211, electrically conducting layer 230, and second metal connection layer 222 respectively. FIGS. 2 A and B are cross sections along the lines A and B in FIGS. 2 C to E.

The connection layer is present to provide better electrical connection to HTS cables (by soldering or direct contact).

The electrically conducting layer is divided into several conductive regions. These regions come in two types. The square regions 231 (though they may be any shape in practice) are connected by conductive links 206 only to one of the metal connection layers. These regions do not affect the electrical properties of the partially insulating layer, but provide a thermal path through the respective insulating layer. By varying the size of these regions and the number of connections between them and the metal connection layer, the thermal properties of the partially insulating layer can be varied independently of the electrical properties.

Figure 2A:
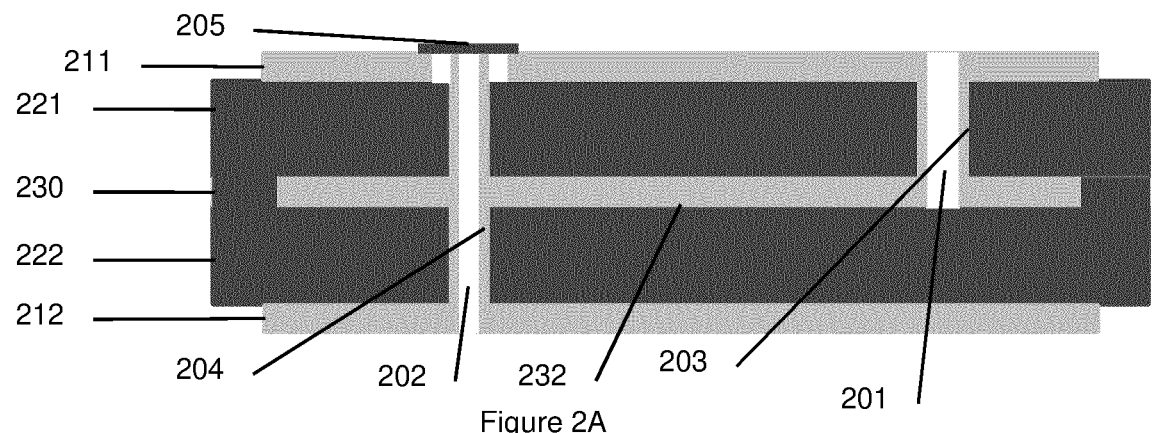
FIGS. 2A to E show a partially insulating layer for an HTS coil.
Figure 2B:
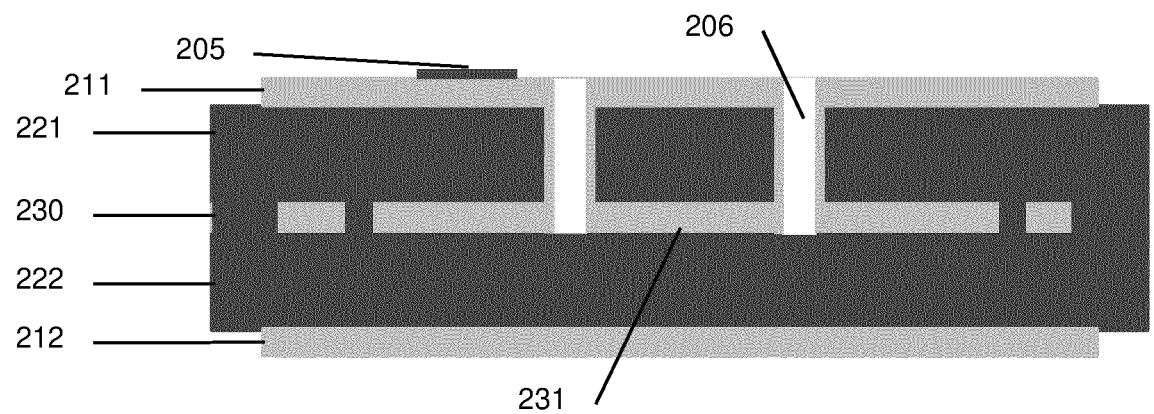
Figure 2C:
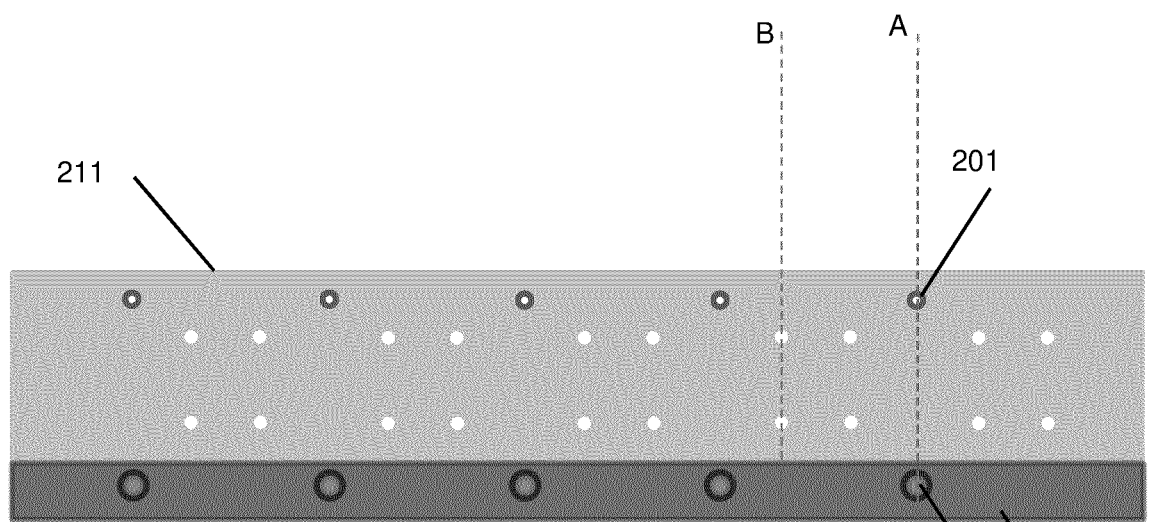
Figure 2D:
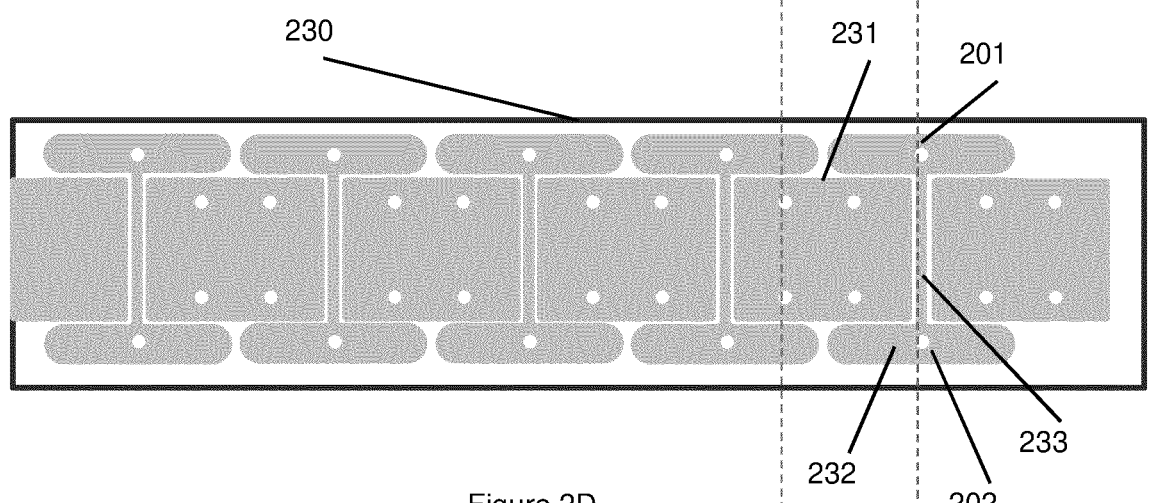
Figure 2E:
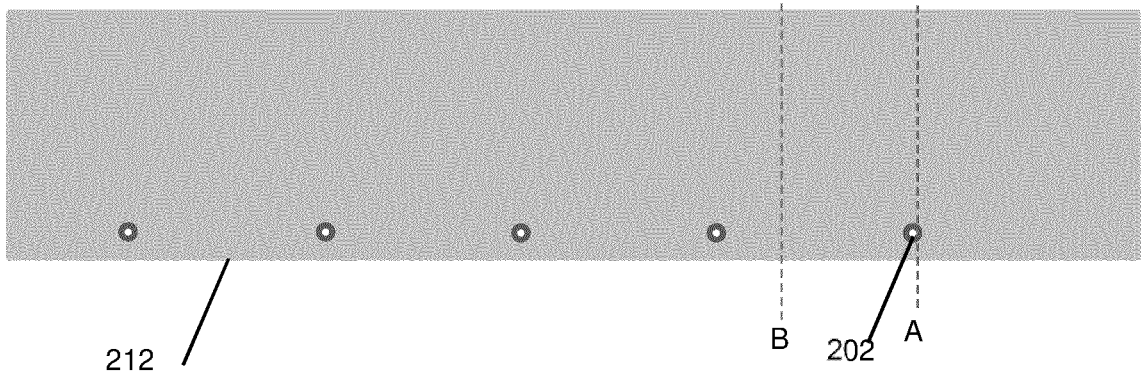

The other regions 232 each connect the first metal connection layer 211 to the second metal connection layer 212, via windows 201, 202 in the first insulating layer 221 and the second insulating layer 222 respectively. The resistance between the windows can be controlled by varying the geometry of the regions 232—e.g. where the region 232 contains an elongated track 233 as shown in FIG. 2B, increasing the width of the track would reduce the resistance between the windows, and increasing the length of the track (e.g. by providing a non-linear track, or by moving the windows) would increase the resistance between windows. The resistance of the entire partially insulating layer can be controlled by both varying the resistance of each connection between windows, and varying the number of such connections along the partially insulating layer.

The windows 201 in the first insulating layer are formed by drilled holes through the first connection layer and the first insulating layer, which are then plated with metal 203 (or other electrically conductive material) to connect the first connection layer 211 and the electrically conductive layer 230. The windows 202 in the second insulating layer are formed by drilling a hole 202 through all of the layers, which is then plated with metal 204 (or other electrically conductive material). To prevent a connection being formed to the first connection layer through the windows 202 of the second insulating layer, the first connection layer is etched around the window 202 to electrically isolate it, and an insulating cap 205 is placed on the end of the window 202 to ensure no bridging occurs due to soldering or contact with the HTS cable.

As an alternative, the windows 202 may instead be drilled from the other side of the partially insulating layer, such that they pass through the second connection layer, second insulating layer, and electrically conducting layer, and do not pass through (or do not pass completely through) the first insulating layer. As a further alternative, all the windows may be formed from holes which pass through all layers, with etching of the second connection layer and an insulating cap on the second connection layer being used for windows 201 of the first insulating layer.

This implementation and related examples are further described in co-pending application PCT/GB2019/050275.

The use of partial insulation will significantly extend the time available to detect a quench, when compared to an equivalent non-insulated coil. However, there is still a need for quench detection methods which are fast enough to detect a hotspot forming in the coil in good time so that countermeasures can be used before damage to the magnet becomes inevitable.

When current in part of the HTS cable of the coil approaches the critical current of the HTS cable, some of the current will leave the HTS and begin to flow through the stabiliser layers of the cable. At this point current will begin to flow through the resistive and inductive links forming the partial insulation between the HTS turns. The PCB fabricated partial insulation facilitates precise layout and design of the linking tracks allowing for precise setting of the turn-to-turn resistance and linking track inductance.

The present disclosure is focused on detecting that current flow, and using that detection to detect when current sharing is starting to occur in the HTS magnet. Detection of this current sharing mode can be used as an advanced warning of a quench (or potential quench—as used herein, "quench detection" includes the detection of imminent quenches or conditions likely to cause a quench).

Figure 3:
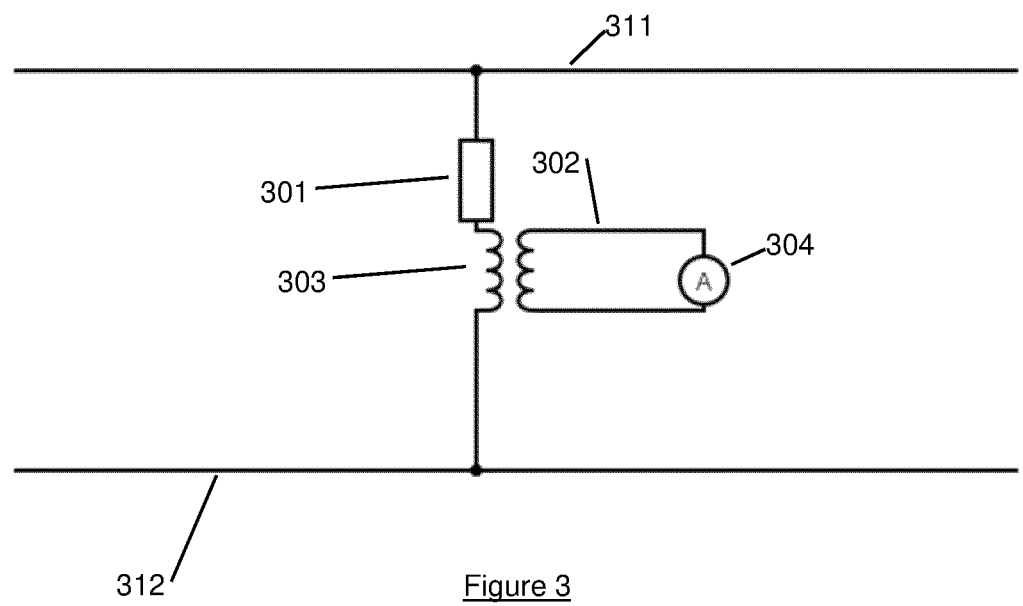
FIG. 3 shows a circuit diagram illustrating the principle of an exemplary partially insulating layer.

The principle is shown schematically in FIG. 3, which is a circuit diagram representing a partially insulating layer. The partially insulating layer has a first track, or "linking track" 301, which connects the HTS cables 311, 312 on either side of the partially insulating layer (equivalently to the tracks 233 in FIG. 2). The partially insulating layer also has a second track, or "pickup track", 302, which is electrically insulated from the HTS cables 311, 312, and is inductively coupled to the first track (represented by the transformer 303). The second track 302 is connected to a current monitor 304. Note that while the resistor and transformer are shown separately in FIG. 3, in the examples below the resistance and inductive coupling arise due to the length and shape of the track itself—i.e. the resistor and transformer need not be provided as separate components.

Due to the inductive coupling between the first and second tracks, any change in the current of the first track (e.g. due to a quench) will cause a corresponding change in the current of the second track. This can then be detected by the current monitor, and the measurements from the current monitor can be used by the controller of the magnet to detect a quench.

Various alterations may be used to improve the sensitivity of the quench detection. For example, the linking and pickup tracks may be shaped to provide greater inductive coupling, e.g. as coils which share a common axis. Multiple pickup tracks may be provided (each corresponding to a separate linking track), and connected in parallel to each other and to the current monitor, such that the current monitor measures the total current induced in all the pickup tracks.

Figure 4A:
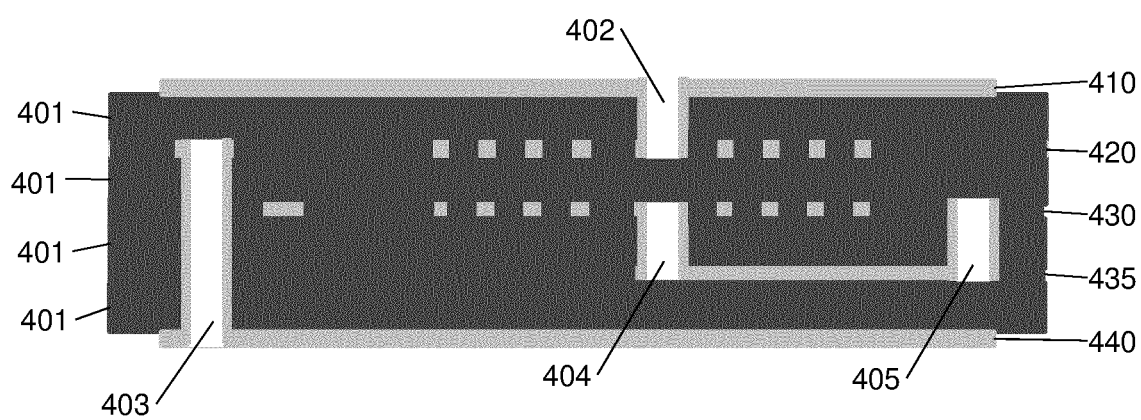
Figure 4E:
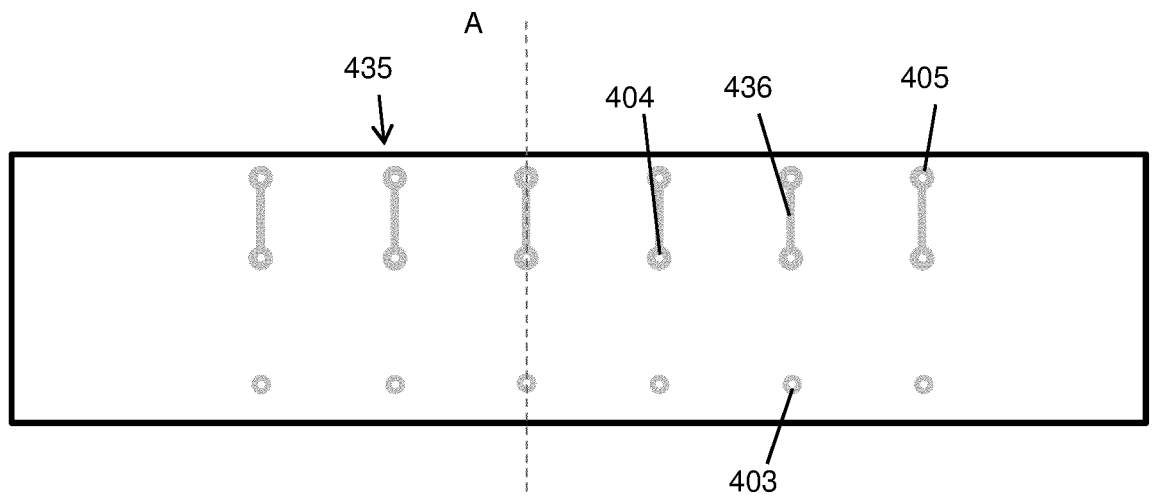
Figure 4F:
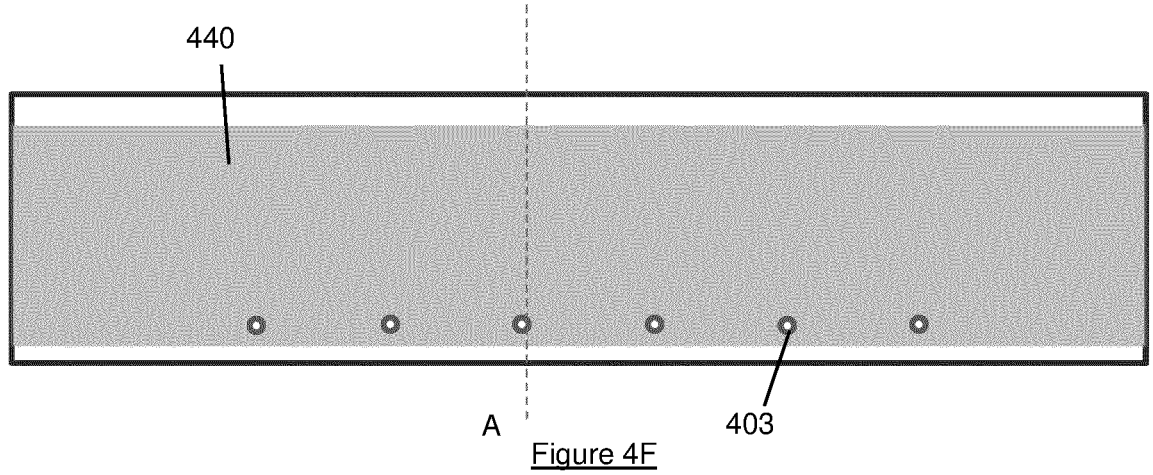

FIGS. 4 A to F show an exemplary partially insulating layer implementing the circuit of FIG. 3. The partially insulating layer comprises eleven layers, of which there are 6 layers containing electrically conducting elements, each separated by an insulating layer 401 (which may be either an insulator on which the electrically conducting layers are printed, e.g. Kapton™ tape, or an insulating adhesive). The layers containing electrically conducting elements are, in order:

A first metal connection layer 410, shown in FIG. 4B.
A linking track layer 420, shown in FIG. 4C.
A pickup track layer 430, shown in FIG. 4D.
A pickup track connection layer, 435, shown in FIG. 4E.
A second metal connection layer 440, shown in FIG. 4F.
FIG. 4A is a cross section along the line A-A in FIGS. 4B to F.

The first and second metal connection layers 410, 440 are substantially the same as those for the previous example—i.e. they are in place to facilitate electrical connection with the HTS cables.

The linking track layer contains several linking tracks 421, formed in this examples as spirals 422 having a tail 423. The centre of the spiral 422 connects to a conductive link 402 which extends through the insulating layer to connect the linking track 421 to the first metal connection layer, and the opposite end of the tail 423 connects to a conductive link 403 which connects the linking track 421 to the second metal connection layer. The conductive links may be formed as holes coated in metal, as with the previous example.

The pickup track layer 430 contains a pickup track 431 corresponding to each of the linking tracks 421. Each pickup track is a spiral of the same dimensions as the corresponding linking track 421, and located directly beneath it. Each pickup track is connected to a rail 432 at the outside of the spiral, and to a rail 433 via the inside of the spiral, by way of a conductive link 404 which connects the inside of the spiral to a track 436 in the pickup track connection layer 435, and a conductive link 405 which connects the track 436 to the rail 433.

The connection of the pickup tracks 431 to the rails 432, 433 ensures that the pickup tracks 431 are connected in parallel. This means that, when the rails 432, 433 are connected via a current meter (not shown, but the rails have pads 434 which extend to the edge of the layer to allow connection to rails of other sections of partially insulating layer, or to the current meter), the current measured by the current meter will be the sum of the currents in the pickup tracks.

The conductive links 403 between the linking track layer and the second metal connection layer also pass through the pickup track layer and the pickup track connection layer, but they are not electrically connected to other elements in those layers.

To avoid interference, the linking and pickup tracks should be arranged such that they do not significantly couple to the magnetic field of the magnet, e.g. having a negligible cross section perpendicular to the local magnetic field. This can be achieved by having them in the plane of the partially insulating layer, as shown in the above examples, but other orientations are also possible.

Figure 5:
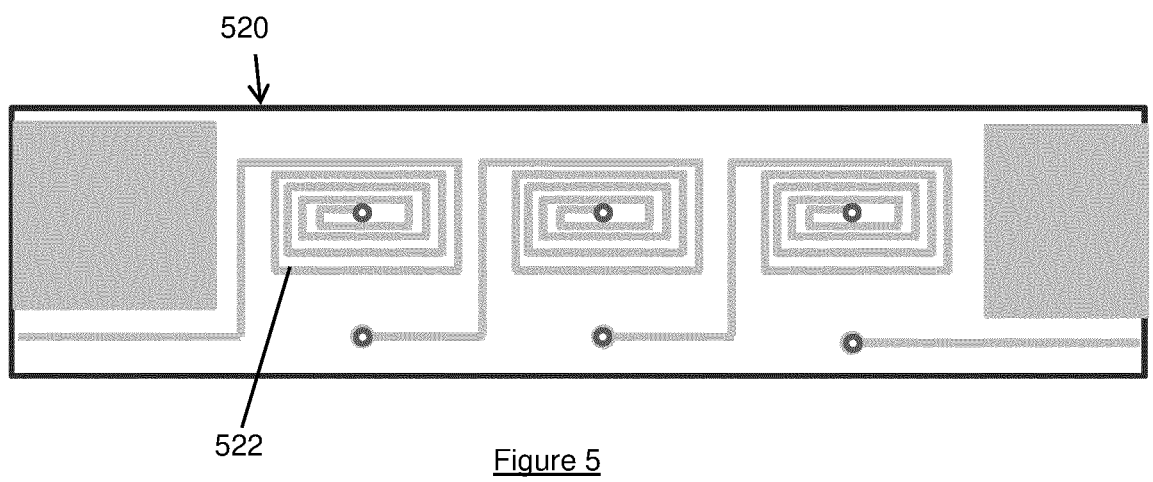
FIG. 5 shows an alternative coil structure.

FIG. 5 shows an alternative arrangement for the linking tracks (which may also be applied to the pickup tracks). Instead of providing curved spiral coils as in FIG. 4C, the linking tracks in the linking track layer 520 (which may be substituted for the linking track layer 420 is designs) are provided as square coils 522.

Figure 6A:
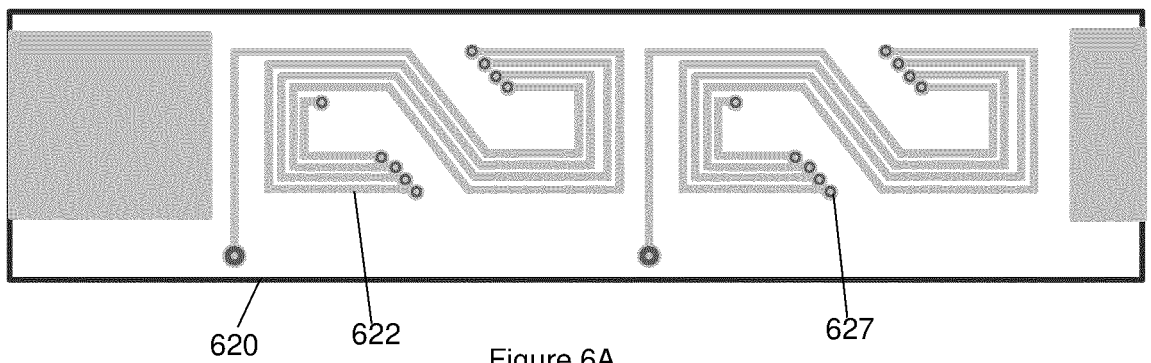
FIGS. 6A and 6B show a further alternative coil structure.
Figure 6B:
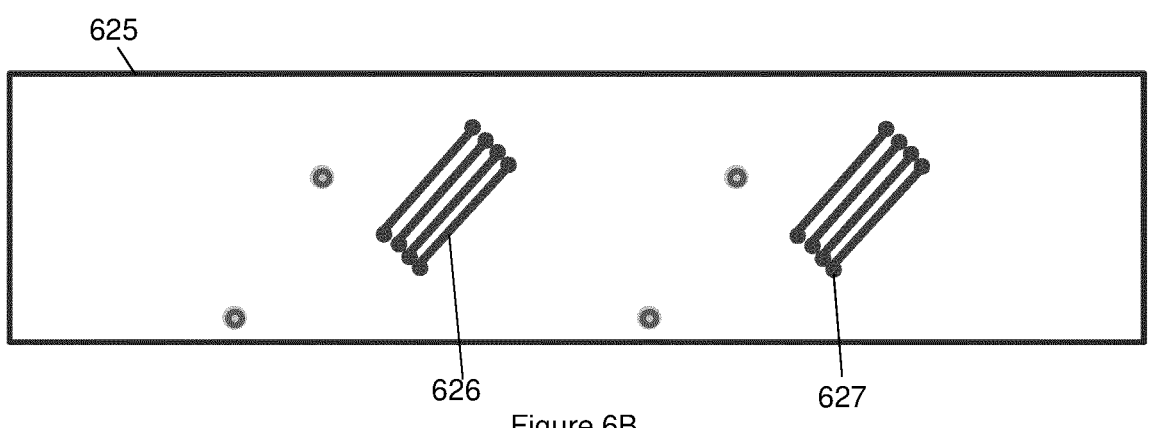

FIGS. 6A and 6B show a further alternative arrangement for the linking tracks. The linking track layer 420 of FIG. 4A is replaced by first and second linking track layers 620, 625. The linking tracks are formed as "butterly coils" in a "figure-8" pattern. Due to this pattern containing a region where the tracks would cross themselves, it should be arranged in two layers to avoid shorts—one such arrangement is shown in FIGS. 6A and 6B, with the main part of the butterly coil 622 provided on the layer 620, and a crossing tracks 626 provided on a separate layer 625, with conductive links 627 between the crossing tracks and the main part of the butterfly coil. Other arrangements which avoid a short are possible, and could be easily envisioned by the skilled person.

The coil designs in FIGS. 4 to 6 are by way of example only. Any arrangement which results in the pickup tracks being sensitive to changes in the current of the linking tracks (i.e. indictively coupled to the linking tracks) can be used to detect current leakage through the partially insualting layer.

Figure 7A:
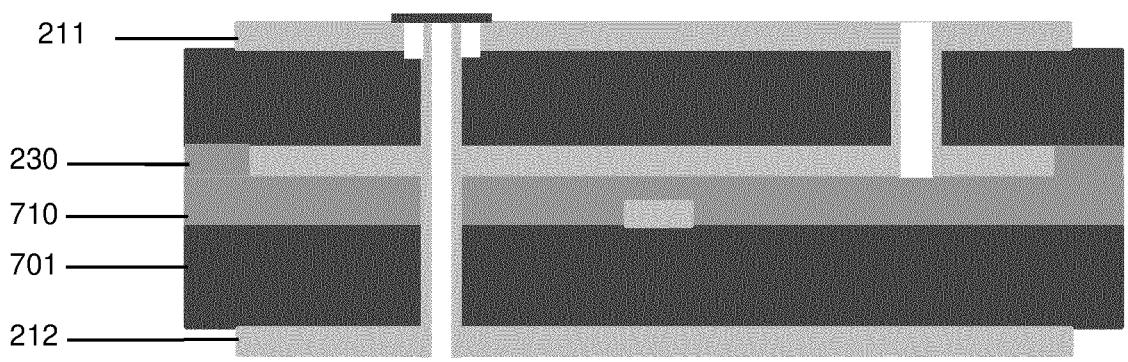
FIGS. 7A and 7B show an alternative construction of a partially insulating layer.
Figure 7B:
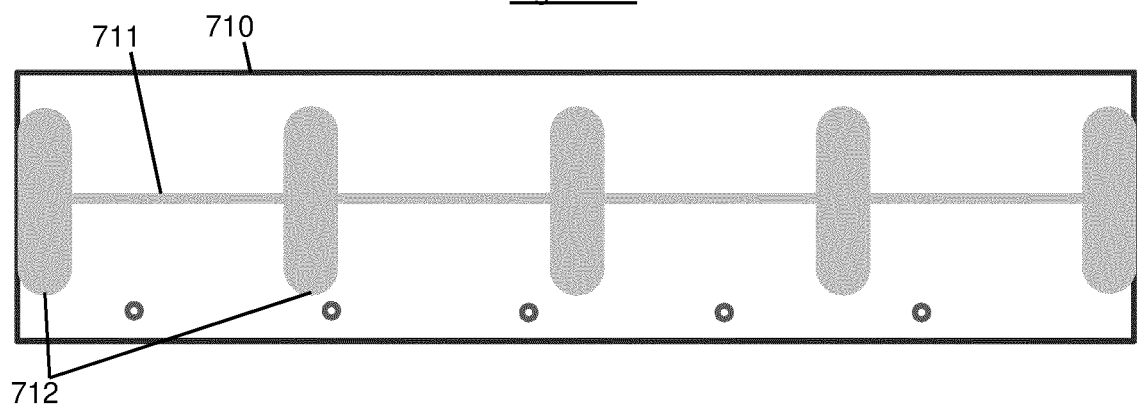

An alternative design is shown in FIGS. 7 A and B. FIG. 7 shows a partially insulating layer 701 comprising:
a first metal connection layer (identical to layer 211 in FIGS. 2A to E);
an linking track layer (identical to layer 230 in FIGS. 2A to E);
a pickup track layer 710; and
a second metal connection layer (identical to layer 212 in FIGS. 2A to E).

The layers are separated by insulating layers 701, as in the previous examples.

The pickup track layer 710 comprises a pickup track 711 which extends along the coil, in order to couple with the spiral path of the HTS magnet, and conductive links 712 which connect the linking track layer to the outer interface layer (without connecting to the pickup track). The pickup track 711 has connection pads 712 at each end, which are then connected to a voltmeter. The pickup track 711 is in close proximity to the coil conductor and will inductively couple with it. Voltages that appear across the coil will also appear on this co-wound track, and will be detected by the voltmeter. Further connection pads may be provided along the length of the partially insulating layer, allowing it to be easily made in bulk and then cut to length as required for the magnet (i.e. ensuring that a connection pad can be available at the end of the partially insulating layer, whatever the size of the HTS coil).

The partially insulating layers described above may be made using a flexible PCB manufacturing process, i.e. starting with one of the insulating layers, applying copper to its upper and lower surface, and etching the copper to form two adjacent electrically conducting layers. Further layers may be added by applying further insulating layers and copper layers to the stack (where the insulating layer may be an adhesive used to bond the next copper layer to the stack) and then etching, or by bonding together further copper-clad-and-etched insulating layers (e.g. to form a copper-insulator-copper-adhesive-copper-insulator-copper construction). Vias can be drilled through the appropriate copper and insulating layers, and then coated with copper to provide connection between copper layers (i.e. the conductive links of the examples above). If a via passes through a layer which it should not be electrically connected to, then a region of that layer around the via may be etched to ensure a clear insulating space between the via and electrically conductive components of the layer. Where this occurs on an external layer (e.g. metal connection layers 410, 440), an insulating cap may be affixed to the end of the via to prevent shorts due to soldering or connection to the HTS cable.

While the above refers to a single "partially insulating layer" for the coil, it will be appreciated that this may be made up of several sections connected end-to-end, either with connections between the pickup track layers, or with a separate current detector for each section of pickup track layer (or some combination—e.g. a current detector for every N sections).

The partially insulating layer may have the same width as the HTS tape. The method of winding the HTS pancake coils may involve drawing HTS tape from multiple spools to form a "cable" of many tapes which collect at the coil. The partially insulating layer would be fed in with the multi-tape cable to form part of the winding. The resulting coil structure would be a multi-tape cable interleaved with the partially insulating layer. The tapes and partially insulating layer outer faces are pre-wetted with flux then the wound pack is consolidated with by flooding with solder. The coil faces are cleaned afterward to ensure the partially insulating layer layers are not by-passed by solder bridges from turn-to-turn.

Once wound and consolidated the end of the partially insulating layer on the outer diameter of the coil is peeled back slightly so that a pair of fine wires can be attached to the contact pads at the end of the pick-up coil layer. This twisted pair of wires links to a current transducer used to detect the signal of current flowing in the leaky insulation.

It will be appreciated that the above examples may be modified in simple ways without departing from the principle of the disclosure (i.e. the provision of pickup tracks inductively coupled to either the HTS coil, or the resistive paths through the partially insulating layer). For example, the connection layers on the outer surfaces of the partially insulating layers may be omitted, and connection between the linking track layer and the HTS cables made directly through the conductive links, or the partially insulating layer may have the linking and pickup tracks disposed within a solid insulating body rather than the multi-layered structure presented above.

The invention claimed is:

1. A current carrying assembly for use in high temperature superconducting, HTS, magnet coil, the current carrying assembly comprising a partially insulating layer and first and second HTS cables;
the partially insulating layer comprising:
an insulating body having within it:
a set of linking tracks, wherein each linking track is electrically conductive and is electrically connected to first and second surfaces of the partially insulating layer, in order to provide an electrical path between said first and second surfaces;
a set of pickup tracks, wherein each pickup track is electrically conductive and is inductively coupled to a respective linking track, and electrically isolated from the first and second surfaces;
wherein the first and second HTS cables are on the respective first and second surfaces of the partially insulating layer; and
wherein each of the pickup tracks is electrically connected to electrical contacts on surfaces of the partially insulating layer other than the first and second surfaces.

2. A current carrying assembly according to claim 1, wherein the set of pickup tracks is connected in parallel, and is configured to connect in parallel to the current measuring device.

3. A current carrying assembly according to claim 2, wherein the pickup tracks are arranged such that, when the partially insulating layer is connected end-to-end to an identical further partially insulating layer, the pickup tracks on both partially insulating layers are connected in parallel with each other and with the current measuring device via the electrical contacts.

4. A current carrying assembly according to claim 1, wherein each pickup track and each linking track has a section which is a spiral.

5. A current carrying assembly according to claim 1, wherein each pickup track and each linking track has a section which is a butterfly coil.

6. A current carrying assembly according to claim 1, wherein each linking track is electrically connected to said first and second surfaces by vias which are coated in an electrical conductor.

7. A current carrying assembly according to claim 1, wherein the partially insulating layer is formed as a plurality of layers, each layer being separated by insulating material, the layers comprising:
a linking track layer having within it the linking tracks; and
a pickup track layer having within it the pickup tracks;
wherein electrical connection between the linking tracks and the first and second surface is achieved by vias through the insulating material, said vias containing electrically conductive material.

8. A current carrying assembly according to claim 1, and comprising on each of the first and second surface, an electrically conductive connection layer electrically connected on one side to the linking tracks and on the other side to the respective HTS cable.

9. An high temperature superconducting, HTS, field coil comprising a one or more current carrying assemblies according to claim 1, wherein the HTS cables are arranged to form turns, and the partially insulating layers are arranged to connect the turns radially.

10. An HTS field coil according to claim 9, wherein the one or more HTS cables and the one or more partially insulating layers are continuously wound to form the turns.

11. An HTS field coil according to claim 9, wherein the one or more HTS cables and the one or more partially insulating layer are arranged in a plurality of sections connected by joints.

12. A tokamak comprising a toroidal field coil which is an HTS field coil according to claim 9.

13. A proton beam therapy, PBT, device comprising an HTS field coil according to claim 9, wherein the HTS field coil is one of:
a field coil of an accelerator of the PBT device;
a dipole or quadrupole magnet of a proton beam steering system of the PBT device.

14. A current carrying assembly for use in a high temperature superconducting, HTS, magnet coil, the current carrying assembly comprising a partially insulating layer and first and second HTS cables;
the partially insulating layer comprising:
an insulating body having within it:
a set of linking tracks, wherein each linking track is electrically conductive and is electrically connected to first and second surfaces of the partially insulating layer, in order to provide an electrical path between said first and second surfaces;
a pickup track, wherein the pickup track is electrically conductive, extends along the length of the partially insulating layer, and is electrically isolated from the first and second surfaces;
wherein the first and second HTS cables are on the respective first and second surfaces of the partially insulating layer; and
wherein the pickup track has electrical contacts on surfaces of the partially insulating layer other than the first and second surfaces.

15. A current carrying assembly according to claim 14, wherein the pickup tracks is arranged such that, when the partially insulating layer is connected end-to-end to an identical further partially insulating layer, the pickup tracks on both partially insulating layers are connected in series with each other and with the voltage measuring device via the electrical contacts.

16. A current carrying assembly according to claim 14, wherein the partially insulating layer is formed as a plurality of layers, each layer being separated by insulating material, the layers comprising:
a linking track layer having within it the linking tracks; and
a pickup track layer having within it the pickup tracks;
wherein electrical connection between the linking tracks and the first and second surface is achieved by vias through the insulating material, said vias containing electrically conductive material.

17. A current carrying assembly according to claim 14, and comprising on each of the first and second surface, an electrically conductive connection layer electrically connected on one side to the linking tracks and on the other side to the respective HTS cable.

18. An high temperature superconducting, HTS, field coil comprising a one or more current carrying assemblies according to claim 14, wherein the HTS cables are arranged to form turns, and the partially insulating layers are arranged to connect the turns radially.

19. A tokamak comprising a toroidal field coil which is an HTS field coil according to claim 18.

20. A proton beam therapy, PBT, device comprising an HTS field coil according to claim 18, wherein the HTS field coil is one of:
a field coil of an accelerator of the PBT device;
a dipole or quadrupole magnet of a proton beam steering system of the PBT device.

\* \* \* \* \*